US00PP21436P2

(12) United States Plant Patent
Hawke

(10) Patent No.: US PP21,436 P2
(45) Date of Patent: Nov. 2, 2010

(54) ***STACHYS* PLANT NAMED 'PINK COTTON CANDY'**

(50) Latin Name: *Stachys officinalis*
Varietal Denomination: Pink Cotton Candy

(75) Inventor: Richard Hawke, Chicago, IL (US)

(73) Assignee: Chicagoland Grows, Glencoe, IL (US)

( * ) Notice: Subject to any disclaimer, the term of this patent is extended or adjusted under 35 U.S.C. 154(b) by 0 days.

(21) Appl. No.: 12/586,653

(22) Filed: Sep. 25, 2009

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner*—Susan B McCormick Ewoldt
(74) *Attorney, Agent, or Firm*—Penny J. Aguirre

(57) ABSTRACT

A new cultivar of *Stachys* plant, 'Pink Cotton Candy', characterized by its flowers that are bright pink and two-toned in color with the upper lip of the petals lighter pink in color than the lower lip of the petals, its combination of newly opened flowers and fading flowers that impart an addition two-tone effect to the inflorescences, its free-flowering habit with an abundance of blooms produces for at least 8 weeks during the summer months, its robust and dense mound of deep green foliage with upright flowering stems arising above the foliage, and its hardiness in U.S.D.A Zones 4 to 8.

2 Drawing Sheets

Botanical classification: *Stachys officinalis*.
Variety denomination: 'Pink Cotton Candy'.

BACKGROUND OF THE INVENTION

The present invention relates to a new and distinct cultivar of *Stachys* plant, botanically known as *Stachys officinalis* 'Pink Cotton Candy' and will be referred to hereinafter by its cultivar name, 'Pink Cotton Candy'. The new cultivar of *Stachys* is a hardy herbaceous perennial grown for landscape use.

'Pink Cotton Candy' was discovered in July of 2002 as a naturally occurring whole plant mutation in the breeder's evaluation garden plot in Glencoe, Ill. The parents of the new cultivar are unknown, however 'Pink Cotton Candy' was discovered growing between unnamed plants of *Stachys officinalis, Stachys officinalis* 'Alba'(not patented) and *Stachys officinalis* 'Rosea' (not patented).

Asexual reproduction of the new cultivar was first accomplished by division in March of 2004 by the Inventor in Glencoe, Ill. It has been determined that the characteristics are stable and reproduced true to type in successive generations.

SUMMARY OF THE INVENTION

The following traits have been repeatedly observed and are determined to be the characteristics of the new cultivar. These attributes in combination distinguish 'Pink Cotton Candy' as a unique cultivar of *Stachys*.

1. 'Pink Cotton Candy' exhibits flowers that are bright pink in color; they are two-tone with the upper lip of the petals lighter pink in color than the lower lip of the petals.
2. 'Pink Cotton Candy' exhibits flowers that fade to a lighter pink color with the combination of newly opened flowers and fading flowers imparting an addition two-tone effect to the inflorescences.
3. 'Pink Cotton Candy' exhibits a free-flowering habit with an abundance of blooms produced for at least 8 weeks during the summer months.

4. 'Pink Cotton Candy' exhibits a robust, dense mound of deep green foliage with upright flowering stems arising above the foliage.
5. 'Pink Cotton Candy' is hardy at least in USDA Zones 4 to 8.

In comparison to the most probable parent plants: *Stachys officinalis* differs from 'Pink Cotton Candy' in having purple flowers, 'Alba' differs from 'Pink Cotton Candy' in having white flowers, and 'Rosea' differs from 'Pink Cotton Candy' in having lighter pink flowers that often fade to white or appear washed out in strong sunlight. 'Pink Cotton Candy' can also be compared to the cultivar 'Saharan Pink' (not patented). 'Saharan Pink' is similar to 'Pink Cotton Candy' in having flowers that exhibit a coloration of two-tones of pink, however 'Saharan Pink' is a seed-strain with a smaller stature, less uniformity in plant habit, produces about 50% less flowers at peak bloom, and produces flowers that are lighter pink in color.

BRIEF DESCRIPTION OF THE DRAWINGS

The accompanying colored photographs illustrate the overall appearance and distinct characteristics of the new *Stachys*. The plants and plant parts depicted in the photographs were taken of plants of 'Pink Cotton Candy' that were four years in age as grown outdoors in a trial garden in Glencoe, Ill.

The photograph in FIG. 1 shows the uniformity in plant habit and the abundance of two-toned bright pink flowers.

Figure 1:
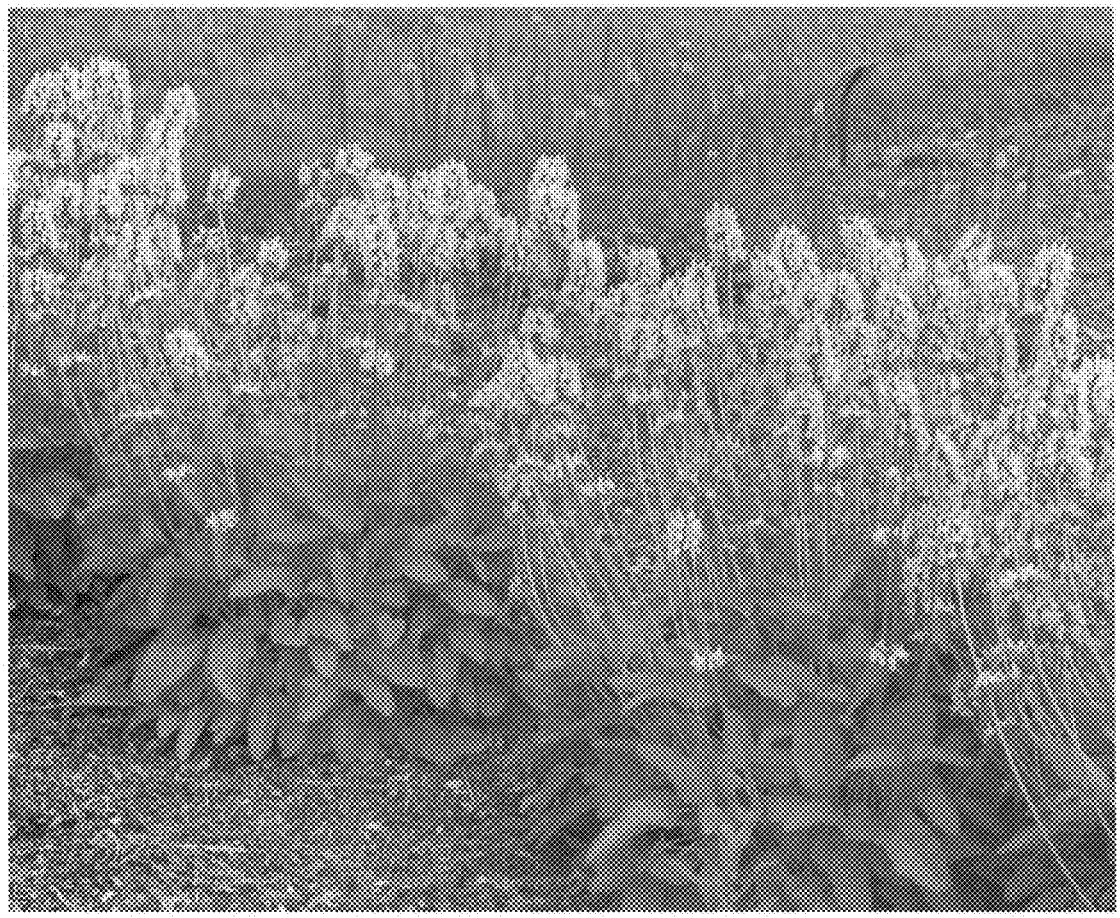
Figure 2:
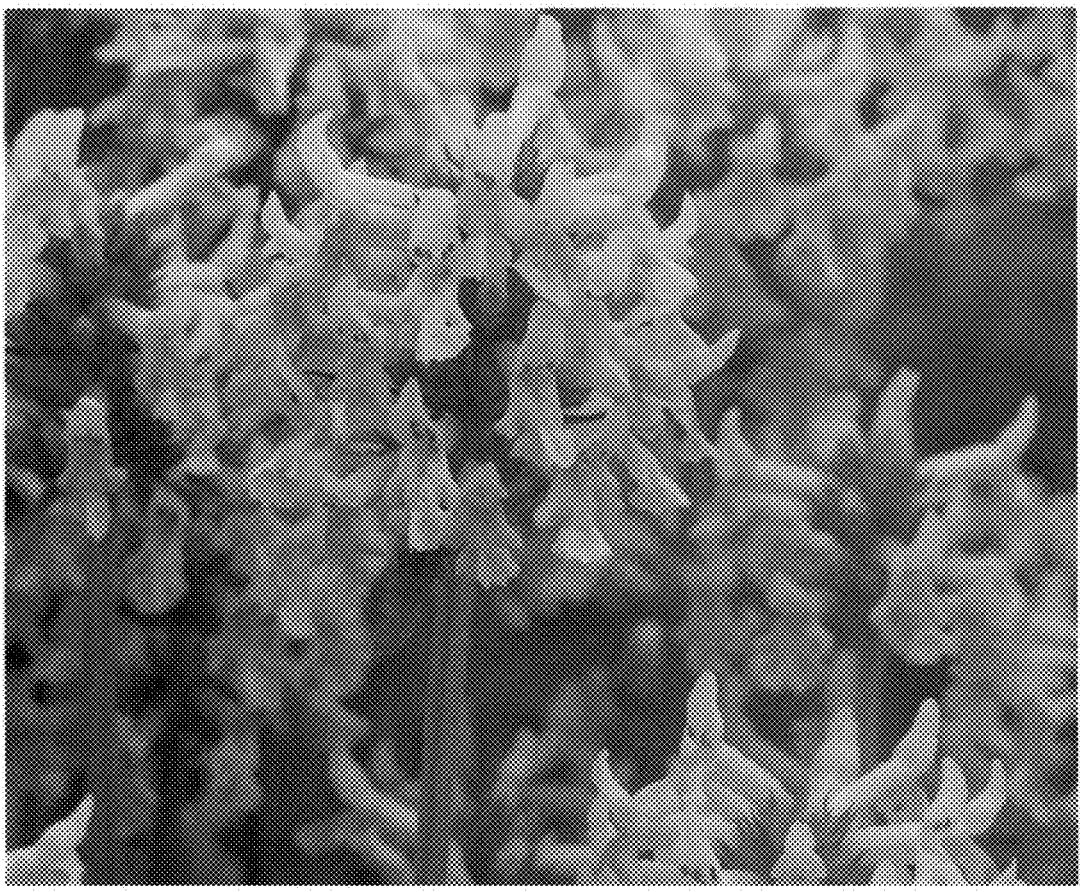

The photograph in FIG. 2 provides a close-up view of an inflorescence. The colors in the photograph may differ slightly from the color values cited in the detailed botanical description, which accurately describe the colors of the new *Stachys*.

DETAILED BOTANICAL DESCRIPTION

The following is a detailed description of two year-old plants of the new cultivar as grown outdoors in a garden in New Hope, Minn. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Blooms for at least 8 weeks, typically blooming from late June or early July through late August.

*Plant habit.*—Herbaceous perennial with a robust, dense mound of deep green foliage with upright flowering stems arising above the foliage.

*Height and spread.*—Matures to about 56 cm in height (28 cm without blooms) and 56 cm in width.

*Hardiness.*—U.S.D.A. Zones 4 to 8.

*Diseases and pests.*—No susceptibility or resistance to diseases or pests has been observed.

*Root description.*—Fibrous.

*Propagation.*—Division.

*Growth rate.*—Moderate.

Stem description (flowering):

*Shape.*—Square.

*Stem color.*—144A to 144B.

*Stem size.*—Average of 2.2 mm in diameter and 56 cm in length (including peduncle).

*Stem surface.*—Pubescent.

*Branching habit.*—Non-branching.

*Stem quantity.*—Average of 20 per plant 2 years in age.

Foliage description:

*Leaf division.*—Simple.

*Leaf arrangement.*—Opposite.

*Leaf shape.*—Basal leaves; ovate-oblong, stem leaves; broadly lanceolate.

*Leaf size.*—Basal leaves; variable with mature leaves up to 8.5 cm in length and 5.5 cm in width, stem leaves; variable with mature leaves up to 7.8 cm in length and 3.5 cm in width.

*Leaf number.*—Average of 85 basal leaves and an average of 2 pairs on stems.

*Leaf base.*—Cordate.

*Leaf apex.*—Basal leaves; rounded, stem leaves; acute.

*Leaf margin.*—Basal leaves; crenate with mucronate tip, about 14 per side on a leaf 8 cm in length, stem leaves; serrate with about 10 per leaf 4.5 cm in length.

*Leaf venation.*—Pinnate, mid rib is 145B on upper surface and 145C on lower surface on both basal and stem leaves.

*Leaf surface.*—Upper surface and lower surface (all leaves); very finely puberulent (glabrous in appearance), lower surface is satiny.

*Leaf internode length.*—Stem leaves; 7 to 10 cm.

*Leaf color.*—New and mature (all leaves) upper surface; 137A to 137B, new and mature (all leaves) lower surface; 137C.

*Petioles.*—Basal leaves; average of 8 cm in length and 2 mm in width, 146A in color, pubescent surface, stem leaves; average of 4.5 cm in length and 1.5 mm in width on lower pair and 5 mm in length and 1.5 mm in length on upper pair, 146A in color, pubescent surface.

*Foliage fragrance.*—None.

Flower description:

*Inflorescence type.*—6 to 8 terminal verticillasters (dense whorls) of bilabiate flowers.

*Lastingness of inflorescence.*—Individual flowers last 2 to 3 days, each verticillaster lasts about 4 weeks.

*Inflorescence size.*—About 4.5 cm in depth and 2.5 cm in diameter.

*Flower type.*—Bilabiate.

*Flower number.*—An average of 30 flowers per verticillaster, 180 to 240 flowers per inflorescence.

*Flower fragrance.*—None.

*Flower buds.*—Oblanceolate in shape, an average of 1.3 cm in length and 4 mm in width at apex, surface is glabrous, color a blend of 73C and 73D with calyx a blend of 138B and 138C.

*Flower size.*—About 1.5 cm in length and about 1.2 cm in diameter.

*Peduncles.*—Range from 3 to 10 cm in length (average of 5 m) and an average of 2.2 mm in width with the internode between verticillaster about 8 mm, surface is densely covered with white hairs, color 144A covered with hairs 144D in color, leaves at base of verticillaster; lanceolate in shape, serrated margins with stiff hairs, both surfaces are puberulent, acute apex, cuneate base, sessile.

*Pedicels.*—None, sessile to peduncle.

*Bracts.*—2 to 4 per flower, lanceolate in shape, an average of 3.5 mm in length and 1.5 mm in width, pubescent surface, cuneate base, aristulate apex.

*Calyx.*—5-pointed, campanulate in shape, about 7.5 mm in length and 4 mm in width, persistent.

*Sepals.*—5, primarily fused with unfused tips, triangular in shape and about 1.5 mm in width and length, 144C to 144D in color with tips 144A, surface is puberulent with longer hairs on margins of tips, aristulate apex, entire margins.

*Petals.*—Fused base with unfused portion spreading and 2-lipped, lower lip; broadly obovate in shape, base is truncate to tube, 3-lobed with a rounded apex on each lobe with center lobe larger, margin is entire on side lobes and irregularly crenate on center lobe, about 6 mm in length and 6 mm in width, color of upper surface is a blend of 73B and 73C with 2 plumose crests on center lobe 68A, color of lower surface is a blend of 73C and 73D, upper lip; ovate in shape, retuse apex, base truncate to tube, margin is entire except for a notch on each side and at the apex, about 6 mm in length and 4 mm in width, color of both surfaces is a blend of 73C and 73D, tube portion; about 1 cm in length and 3 mm in width, color is a blend of 73C and 73D with the base NN155B surface of all segments on both surfaces is puberulent, color of all petals fade to 73D.

Reproductive organs:

*Gynoecium.*—1 Pistil, style is about 8.5 mm in length, 0.3 mm in width and NN155D in color, stigma is bi-fid, about 0.3 mm in diameter and 145D in color, ovary is superior, about 0.5 mm in diameter, translucent and 195B in color.

*Androecium.*—4 stamens, filament is about 9 mm cm in length, adnate to corolla and 73D in color, anthers are globose in shape, about 0.7 mm in diameter, dorsifixed, and 177A in color, pollen is abundant and 162C in color.

*Fruit.*—Fruit and seed production was not observed under the conditions tested.

It is claimed:

1. A new and distinct variety of *Stachys* plant designated 'Pink Cotton Candy' as described and illustrated herein.

* * * * *